US007354771B2

(12) United States Patent
Inoue et al.

(10) Patent No.: US 7,354,771 B2
(45) Date of Patent: Apr. 8, 2008

(54) METHOD OF DETERMINING ABSOLUTE CONFIGURATION OF CHIRAL COMPOUND

(75) Inventors: Yoshihisa Inoue, Toyonaka (JP); Victor Borovkov, Toyonaka (JP); Juha Lintuluoto, Osaka (JP)

(73) Assignee: Japan Science and Technology Corporation, Saitama (JP)

( * ) Notice: Subject to any disclaimer, the term of this patent is extended or adjusted under 35 U.S.C. 154(b) by 328 days.

(21) Appl. No.: 10/148,652

(22) PCT Filed: Dec. 4, 2000

(86) PCT No.: PCT/JP00/08559

§ 371 (c)(1),
(2), (4) Date: May 30, 2002

(87) PCT Pub. No.: WO01/40774

PCT Pub. Date: Jun. 7, 2001

(65) Prior Publication Data

US 2003/0008406 A1    Jan. 9, 2003

(30) Foreign Application Priority Data

Dec. 3, 1999    (JP)    ................................. 11-345538

(51) Int. Cl.
*G01N 21/00*    (2006.01)
(52) U.S. Cl. ...................... 436/164; 435/280; 514/188; 544/4; 544/47; 502/182; 502/226; 549/260; 549/230; 540/604; 546/25
(58) Field of Classification Search ................ 436/164; 435/280; 514/188; 544/4, 47; 502/182, 502/226; 549/260, 230; 540/604; 546/25
See application file for complete search history.

(56) References Cited

U.S. PATENT DOCUMENTS 6,420,553 B1    7/2002    Inoue et al.

FOREIGN PATENT DOCUMENTS

| JP | 02-237939 | 9/1990 |
| JP | 09-255682 | 9/1997 |
| JP | 10-029993 | 2/1998 |

OTHER PUBLICATIONS

Huang et al., "Porphyrins and metalloporphyrins: Versatile circular dichroic reporter groups for structural studies", Published Online Apr. 28, 2000, CHIRALITY, vol. 12, issue 4, pp. 237-235.*
Barry H. Rickman, et al., "A Two-Step Chemical:Chiroptical Method for Determining Absolute Configurations of α-Hydroxy Acids," Tetrahedron vol. 54, p. 5,041-5,064 1998.
Takashi Hayashi, et al., "Molecular Recognition of α, ω-Diamines by Metalloporphyrin Dimer," Tetrahedron Letters vol. 38, p. 1,603-1,606 1997.
Hai-yang Liu, et al., "Chiral linear assembly of amino acid bridged dimeric porphyrin hosts," Chemical Communications p. 1,575-1,576 1997.
Masayuki Takeuchi, et al., "Sugar-boronic acid interactions in the formation of novel chiral porphyrin dimers with various porphyrin-porphyrin angles," Chemical Communications, p. 1,867-1,868 1996.
Victor V. Borovkov, et al., "Temperature Effect on Supramolecular Chirality Induction in Bis (zinc porphyrin)," J. Am. Chem. Soc., vol. 122, No. 18, p. 4,403-4,407, May 10, 2000 (published on Web: Apr. 21, 2000).
Victor V. Borovkov, et al., "Supramolecular Chirogenesis in Bis (zinc porphyrin): An Absolute Configuration Probe Highly Sensitive to Guest Structure," Org. Lett., vol. 2, No. 11, p. 1,565-1,568, Jun. 1, 2000 (published on Web: May 2, 2000).
Masayuki Takeuchi, et al., "Molecular Design of Highly Selective and Sensitive "Sugar Tweezers" from Boronic Acid-Appended μ-Oxo-bis[porphinatoiron (III)]s," Bull. Chem. Soc. Jpn., vol. 71, p. 1,117-1,123 1998.
A. Aida/Mauyu Seiyaku K.K. Sendai Symposium Youshishuu, "Development of a Novel Chirality Sensor having a Memory Function," vol. 9 p. 23-28 1998, with full translation.
XP-001118314, Borovkov, et al., "Efficient Synthesis of Unsymmetrical Transition Metalloporphyrin Dimers under Mild Conditions," Synlett, No. 7, p. 768-770, 1998.
Eiji Yashima, et al., Chirality Assignment of Amines and Amino Alcohols Based on Circular Dichroism Induced by Helix Formation of a Stereoregular Poly ((4-carboxypheny)acetylene) through Acid-Base Complexation, J. Am. Chem. Soc., vol. 119, No. 27, p. 6,345-6,359 1997.
Xuefei Huang, et al., "Zinc Porphyrin Tweezer in Host-Guest Complexation: Determination of Absolute Configurations of Diamines, Amino Acids, and Amino Alcohols by Circular Dichroism," J. Am. Chem. Soc., vol. 120, No. 24, p. 6,185-6,186 1998.
Hiroshi Tsukube, et al., "Chrality probing of amino alcohols with lanthanide complexes *via* induced circular dichroism spectroscopy," J. Chem. Soc., Dalton Trans., p. 11-12 1999.
XP-001117879, Borovkov, et al., "Synthesis of $Zn^-$,$Mn^-$ and $Fe^-$Containing Mono and Heterometallated Ethanediyl-Bridged Porphyrin Dimers," Helvetica Chimica Acta, vol. 82, p. 919-934, 1999.

(Continued)

*Primary Examiner*—Lyle A. Alexander
(74) *Attorney, Agent, or Firm*—Knobbe Martens Olson & Bear LLP

(57) ABSTRACT

The absolute configuration of a chiral compound is determined by (i) coordinating the chiral compound to a metalloporphyrin having a carbon chain-crosslinked porphyrin dimer structure in which one of the two porphyrin rings has at least one ethyl or substituent bulkier than ethyl at at least one of the second peripheral carbon atoms from the carbon atom at the carbon chain crosslink site, and (ii) analyzing the resultant coordination compound by circular dichroism spectrophotometry to determine the absolute configuration of the asymmetric carbon based on the sign of the Cotton effect. The chiral compound has an asymmetric carbon bonded to a basic group capable of coordinating to the metal of the other porphyrin ring of the metalloporphyrin dimer or an asymmetric carbon atom adjacent to the carbon atom bonded to the basic group.

2 Claims, 3 Drawing Sheets

OTHER PUBLICATIONS

Eiji Yashima, et al., "Poly((4-carboxyphenyl)acetylene) as a Probe for Chirality Assignment of Amines by Circular Dichroism," J. Am. Chem. Soc., vol. 117, pp. 11596-11597, 1995.

Stefan Matile, et al., "Porphyrins: Powerful Chromophores for Structural Studies by Exciton-Coupled Circular Dichroism," J. Am. Chem. Soc., vol. 117, pp. 7021-7022, 1995.

Stefan Matile, et al., "Structural Studies by Exciton Coupled Circular Dichroism over a Large Distance: Porphyrin Derivatives of Steroids, Dimeric Steroids, and Brevetoxin $B^{\perp}$," J. Am. Chem. Soc., vol. 118, pp. 5198-5206, 1996.

Yasuaki Kikuchi, et al., "Complexation of Ciral Glycols, Dteroidal Polyols, and Sugars with a Multibenzenoid, Achiral Host As Studied by Induced Circular Dichroism Spectroscopy: Exciton Chirality Induction in Resorcinol-Aldehyde Cyclotetramer and Its Uses as a Supramolecular Probe for the Assignments of Stereochemistry of Chiral Guests," J. Am. Chem. Soc., vol. 114, pp. 1351-1358, 1992.

Tony D. James, et al., "Saccharide Sensing with Molecular Receptors Based on Boronic Acid," Angew. Chem. Int. Ed. Engl., vol. 35, pp. 1910-1922, 1996.

Susumu Arimori, et al., "Sugar-Sensing by Chiral Orientation of Dimeric Boronic-Acid-Appended Porphyrins Which Show Selectivity for Glucose and Xylose," Chem. Lett., pp. 77-78, 1996.

Tomoyuki Imada, et al., "Sugar-induced Chiral Orientation of a Boronic-acid-appended Porphyrin Stack. Correlation between the Absolute Configuration and the CD (Circular Dichroism) Sign," J. Chem. Soc., Chem. Commun., pp. 1557-1558, 1994.

Steffen Zahn, et al., "Absolute Configurations of *N,N*-Dialkyl α-Amino Acids and β-Amino Alcohols from Exciton-Coupled Circular Dichroism Spectra of Cu(II) Complexes," Org. Lett., vol. 1, No. 6, p. 861-864 1999.

\* cited by examiner

B∥:

Achiral

Chiral

B⊥:

Achiral

Chiral

METHOD OF DETERMINING ABSOLUTE CONFIGURATION OF CHIRAL COMPOUND

This application is the U.S. National Phase under 35 U.S.C. §371 of International Application PCT/JP00/08559, filed Dec. 4, 2000, which claims priority to Japanese Patent Application No. 11/345538, filed Dec. 3, 1999. The International Application was published under PCT Article 21(2) in a language other than English.

TECHNICAL FIELD

The present invention relates to a method for determining the absolute configuration of chiral compounds.

BACKGROUND ART

Conventionally, there have been attempts to determine the absolute configuration of external ligands based on the induced Cotton effects revealed by the analysis of circular dichroism (CD) spectrophotometry. For example, the following are reported:

(1) E. Yashima, T. Matsushima, and Y. Okamoto (J. Am. Chem. Soc., 1997, 119, 6345-6359) report on polymers forming a helical structure in the presence of a chiral compound and describe that there is a good correlation between the sign of the Cotton effect in the circular dichroism spectra induced by the ligand (chiral compound) and the absolute configuration of the ligand.

However, since the helical structure is induced by the ion pair formed between the carboxylate group of the polymer side chain and the ammonium group of the ligand, this method can be used for typical monoamines and aminoalcohols but is not applicable to alcohols.

(2) X. Huang, B. H. Rickmann, B. Borhan, N. Berova, and K. Nakanishi (J. Am. Chem. Soc., 1998, 120, 6185-6186) report on circular dichroism induced in a long chain-crosslinked porphyrin diner by a chiral ligand. There is a correlation between the sign of the Cotton effect and the absolute configuration of the ligand. In this system, however, circular dichroism is induced only when one ligand molecule is concurrently coordinated to two porphyrin units. Therefore, this method is useful only for bifunctional compounds such as diamines and aminoalcohols.

(3) M. Takeuchi, T. Imada, and S. Shinkai (Bull. Chem. Soc., Jpn., 1998, 71, 1117-1123) report that a porphyrin dimer having a phenylboronic acid unit exhibits circular dichroism in the presence of a variety of sugars.

This method is applicable only to polyols (polyalcohols) which form a chemical bond with boronic acid, and it is not a method for directly determining the absolute configuration around a specific asymmetric center.

(4) H. Tsukube, M. Hosokubo, M. Wada, S. Shinoda, and H. Tamiaki (J. Chem. Soc., Dalton Trans., 1999, 11-12) report that a tris(β-diketonato) lanthanide complex exhibits circular dichroism in the presence of chiral amino alcohols. In this system, however, monoamines or monoalcohols do not induce chirality.

(5) S. Zahn, and J. W. Canary (Org. Lett., 1999, 1, 861-864) report that the absolute configuration of amino acids and aminoalcohols can be determined based on the circular dichroism of their copper complexes.

However, this method is applicable only to bidentate amino acids and aminoalcohols and can not be used for monoamines or monoalcohols.

As is clear from the above, there have been no reports about a method for determining the absolute configuration of chiral compounds having a wide variety of basic groups, such as monoalcohols.

The X-ray diffraction method is known as a method for determining the absolute configuration of chiral compounds. However, there is a limitation in that this method is applicable only to crystalline compounds.

DISCLOSURE OF THE INVENTION

Figure 1:
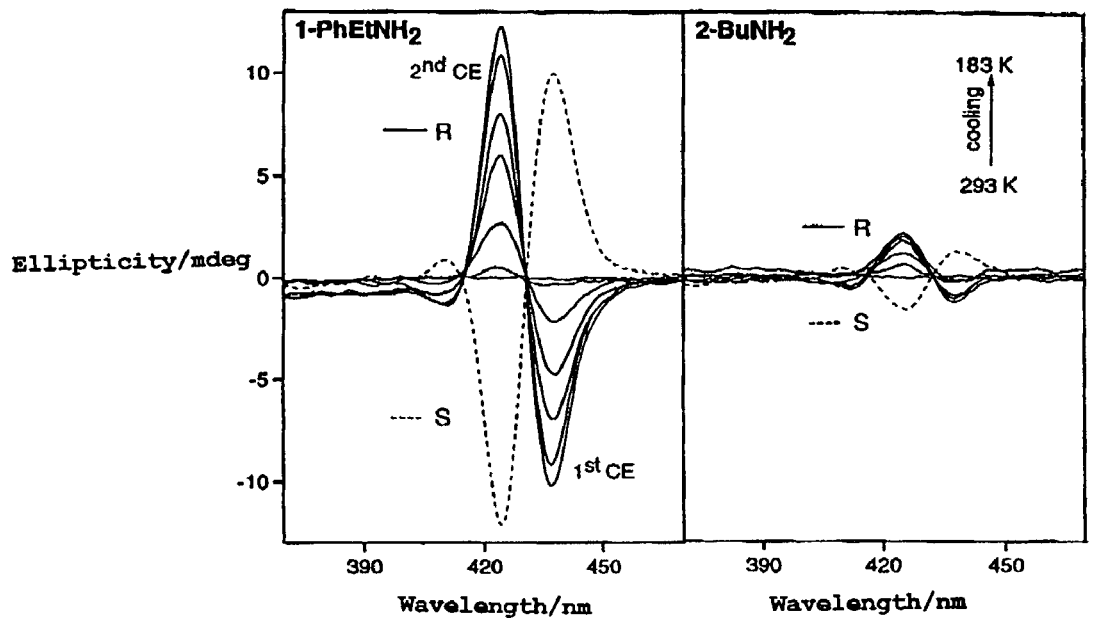
FIG. 1 shows the circular dichroism of a zinc porphyrin dimer induced by a chiral amine.

The principal object of the present invention is to overcome the limits and problems of the prior art and provide a novel general-purpose method for precisely and easily determining the absolute configuration of chiral compounds having a wide variety of basic groups.

The present invention provides the following methods for determining the absolute configuration of chiral compounds:

1. A method for determining the absolute configuration of a chiral compound which comprises:

coordinating the chiral compound to a metalloporphyrin, the metalloporphyrin having a carbon chain-crosslinked porphyrin dimer structure in which one of the two porphyrin rings has at least one ethyl or substituent bulkier than ethyl at at least one of the second peripheral carbon atoms from the carbon atom at the carbon chain crosslink site, the chiral compound having an asymmetric carbon bonded to a basic group capable of coordinating to the metal of the other porphyrin ring of the metalloporphyrin dimer or an asymmetric carbon atom adjacent to the carbon atom bonded to the basic group; and analyzing the resultant coordination compound by circular dichroism spectrophotometry to determine the absolute configuration of the asymmetric carbon of the chiral compound based on the sign of the Cotton effect.

2. The method according to item 1 wherein the ethyl or substituent bulkier than ethyl is 1) a hydrocarbon group having at least 2 carbon atoms, 2) an oxygen-containing substituent, 3) a nitrogen-containing substituent, 4) a halogen atom, or 5) a halogenated hydrocarbon group.

3. The method according to item 1 wherein the chiral compound is 1) a primary amine, 2) a secondary amine, 3) a primary diamine, 4) a secondary diamine, 5) a monoalcohol, or 6) an aminoalcohol.

4. The method according to item 1 or 3 wherein the metalloporphyrin is a compound represented by the following formula (I):

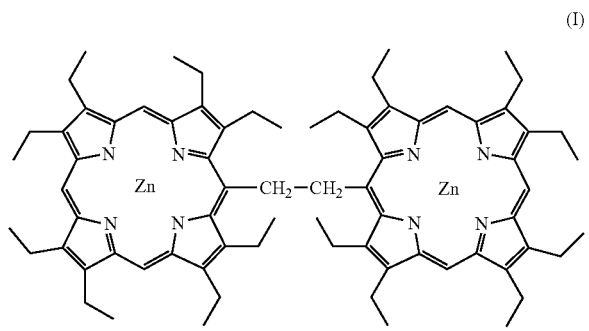

(I)

{μ{{5,5'-(ethane-1,2-diyl)bis[2,3,7,8,12,13,17,18-octa-ethyl-21H,23H-porphyrinato](4-)}-κN$^{21}$, κN$^{22}$, κN$^{23}$, κN$^{24}$, κN$^{21'}$, κN$^{22'}$, κN$^{23'}$, κN$^{24'}$}}dizinc.

The present invention uses circular dichroism (CD) spectrophotometric analysis as described above. In this analysis, the sign of the induced Cotton effect is determined by the absolute configuration of the asymmetric carbon of the external ligand. According to the CD exciton-chirality method (Harada, N.; Nakanishi, K.; Circular Dichroic Spectroscopy-Exciton Coupling in Organic Stereochemistry; University Science Books; Mill Valley, 1983., Nakanishi, K.; Berova, N. In Circular Dichroism; Principles and Applications; Woody, R., Ed; VCH Publishers; New York, 1994; pp. 361-398), a clockwise orientation of two interacting electronic transition moments produces positive chirality, while a counterclockwise orientation leads to negative chirality.

The present invention was accomplished based on the finding that there is a specific correlation between the sign of the Cotton effect and the absolute configuration of the asymmetric carbon of a chiral compound (R-isomer or S-isomer) as a ligand.

The basic principle of this determination of the absolute configuration is described below with reference to the case of zinc porphyrin represented by formula (I):

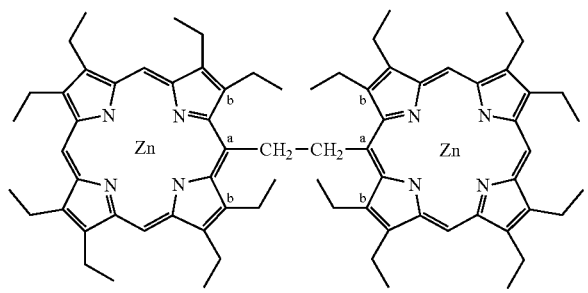

(I)

{μ{{5,5'-(ethane-1,2-diyl)bis[2,3,7,8,12,13,17,18-octa-ethyl-21H,23H-porphyrinato](4-)}-κN$^{21}$, κN$^{22}$, κN$^{23}$, κN$^{24}$, κN$^{21'}$, κN$^{22'}$, κN$^{23'}$, κN$^{24'}$}}dizinc.

This zinc porphyrin has a porphyrin dimer structure in which one of the porphyrin rings has two ethyl groups (—CH$_2$CH$_3$) each bonded to the second peripheral carbon atoms (b), (b) from the carbon atom (a) at the crosslink site crosslinked by an ethylene chain (—CH$_2$—CH$_2$—).

Of course, in the present invention, it is also possible to use a metalloporphyrin which has, in place of the above ethylene chain, a carbon chain having a suitable number of carbon atoms (preferably, a C$_{2-3}$ carbon chain) such as an alkylene chain or the like, the metalloporphyrin ring having at least one bulky substituent in place of at least one of the ethyl groups bonded to the porphyrin ring at the sites (b), (b).

The present inventors already found that a zinc octaethylporphyrin dimer (ZnD) as above undergoes a conformational change from syn to anti upon coordination of an alcohol or an amine such as those represented by the following formulas:

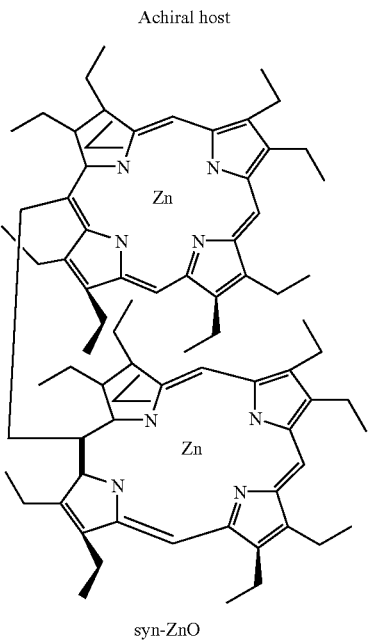

Figure 2:
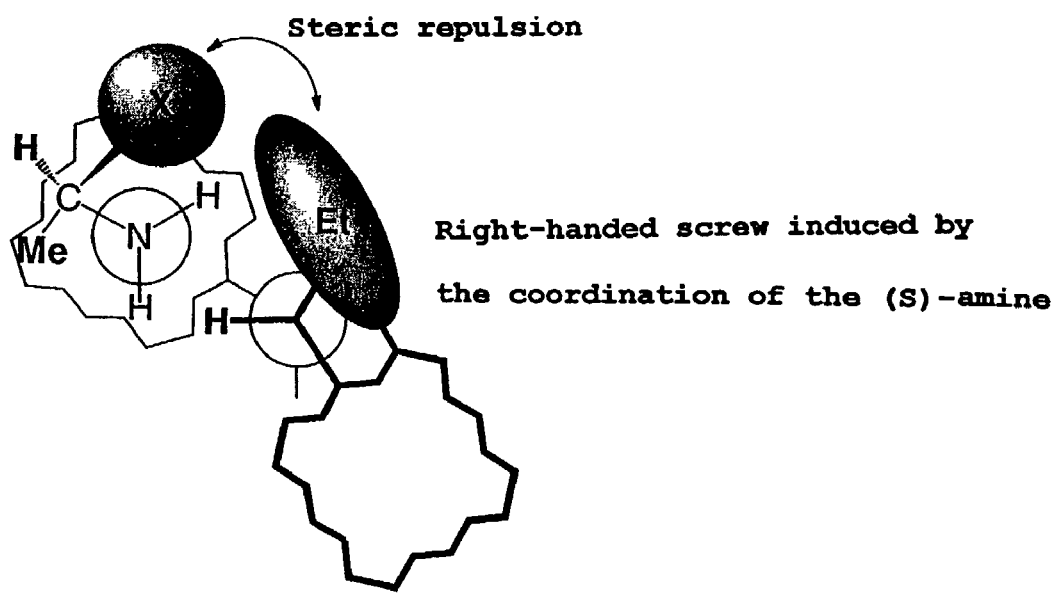
FIG. 2 is a schematic diagram showing the mechanism of asymmetric induction in a zinc porphyrin dimer.

Further, the inventors newly found that upon coordination of a chiral alcohol or a chiral amine, asymmetry is induced in the anti conformer, whereby circular dichroism is exhibited as shown in FIG. 1. The mechanism of asymmetric induction is illustrated in FIG. 2. Thus it can be understood that the porphyrins' orientation is twisted by the steric hindrance between the ethyl group (Et) of the porphyrin and the bulkiest substituent (X) bonded to the α carbon of the ligand, and the exciton interaction between the porphyrin rings produces circular dichroism.

The correlation between the absolute configuration (R-isomer or S-isomer) of a ligand and the sign of the Cotton effect is demonstrated, for example, in Table 1. Table 1 indicates that there is a correspondence between the sign of the Cotton effect and the steric configuration around the α carbon of amino or hydroxyl groups. As shown in FIG. 1, the peak occurring at a shorter wavelength shows the second Cotton effect, whereas the peak at a longer wavelength shows the first Cotton effect. The signs at the peaks may be positive or negative. For example, in the case of 1-phenyl-ethylamine shown in FIG. 1, when the absolute configuration is (R), the second Cotton effect is positive and the first Cotton effect is negative. When the absolute configuration is (S), these signs are reversed. That is, when the first Cotton effect is positive, the absolute configuration of the chiral compound is (S). When the first Cotton effect is negative, the absolute configuration of the chiral compound is (R). Table 1 shows that this correspondence exists in many chiral compounds. These results prove that the above assumption about the mechanism of chirality induction is correct. Based on this correspondence, it is also possible to determine the absolute configuration of chemical compounds whose absolute configuration is unknown.

TABLE 1

Assignment of absolute configuration of chiral amines and alcohols

| Ligand | Absolute configuration and sign of ligand | Second Cotton ($B_\perp$ transition) | First cotton ($B_{II}$ transition) |
|---|---|---|---|
| 2-Buthanol | (R)-(−) | + | − |
| | (S)-(+) | − | + |
| 1-Phenylethanol | (R)-(+) | + | − |
| | (S)-(−) | − | + |
| 2-Buthylamine | (R)-(−) | + | − |
| | (S)-(+) | − | + |
| 1-Phenylethylamine | (R)-(+) | + | − |
| | (S)-(−) | − | + |
| 1-(1-Naphthyl)ethylamine | (R)-(+) | + | − |
| | (S)-(−) | − | + |
| 1,2-Diaminocyclohexane | (1R,2R)-(−) | + | − |
| 1-Amino-2-propanol | (R)-(−) | + | − |
| | (S)-(+) | − | + |
| 2-Amino-4-methyl-1-pentanol | (R)-(−) | + | − |
| | (S)-(+) | − | + |
| 1-Cyclohexylethylamine | (R)-(−) | + | − |
| | (S)-(+) | − | + |
| N-methyl-1 phenylethylamine | (R)-(+) | + | − |
| | (S)-(−) | − | + |
| 2-Methyl-1-butylamine | (S)-(−) | − | + |
| Bornylamine | (1R,2S)-(+) | − | + |
| 1,2-Diphenylethylene-diamine | (1R,2R)-(+) | + | − |
| | (1S,2S)-(−) | − | + |

Figure 3:
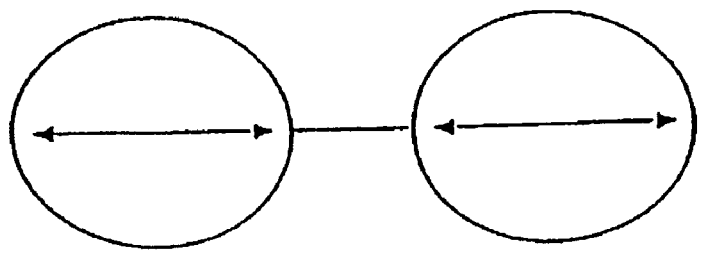
FIG. 3 illustrates the moment directions of the maximum absorption band of a porphyrin dimer.
Figure 3:
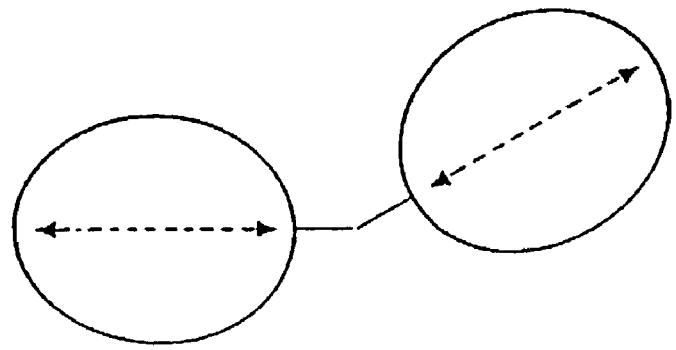
Figure 3:
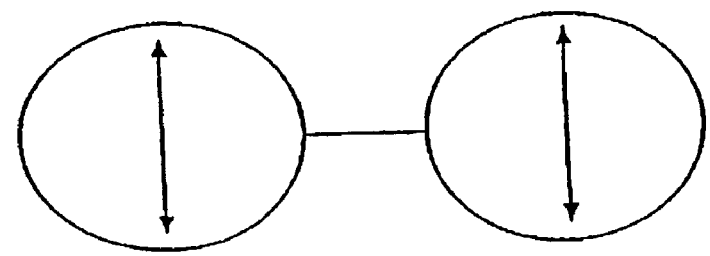
Figure 3:
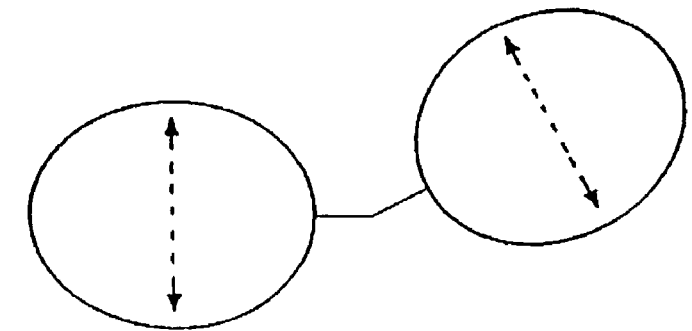

In Table 1, the $B_{II}$ transition is a transition occurring when the moments of two porphyrin rings are aligned in the direction of bonding the porphyrin rings and the resulting absorption band is B-band. The $B_\perp$ transition is a transition occurring when the moments of two porphyrin rings are in directions perpendicular to the direction of bonding the porphyrin rings and the resulting absorption band is B-band (see the solid line in FIG. 3). In both the $B_{II}$ transition and the $B_\perp$ transition, the directions of moments of the two porphyrin rings of a chiral porphyrin dimer are slightly misaligned with respect to each other, as compared to the achiral porphyrin dimer (see the dotted line in FIG. 3).

As described above with respect to zinc porphyrin, the invention makes it possible to determine the absolute configuration of the asymmetric carbon of chiral compounds.

The metalloporphyrin used in the method of the invention has a carbon-chain crosslinked porphyrin dimer structure in which one of the two porphyrin rings has ethyl or substituent bulkier than ethyl at at least one of the second peripheral carbon atoms from the carbon atom at the carbon chain crosslink site (i.e., the carbon atom bonded to the crosslinking carbon chain, on one of the porphyrin rings).

The ethyl or substituent bulkier than ethyl means a substituent whose volume is as large as or larger than ethyl. Examples of such substituents include 1) hydrocarbon groups having at least 2 carbon atoms such as ethyl, propyl, butyl and the like, 2) oxygen-containing substituents such as ester groups (e.g., methyl ester, ethyl ester), carboxymethyl and the like, 3) nitrogen-containing substituents such as amino, amide, 2-aminoethyl and the like, 4) halogen atoms such as —Cl, Br—, —F and the like, and 5) halogenated hydrocarbon groups such as chloroethyl and the like. The same or different substituents may be bonded to a metalloporphyrin.

Any of a variety of metal porphyrin compounds can be used as the metalloporphyrin as long as the metal is a 6-coordinate metal. Such metals are not limited to zinc but also include Fe, Mn, Ru, etc. The two metals of the dimer may be the same or different.

The metalloporphyrin used in the present invention can be synthesized by known methods (e.g., Japanese Unexamined Patent Publication No. 255790/1999). The use of zinc porphyrin is especially preferred in the present invention.

The chiral compound whose absolute configuration can be determined by the method of the invention is, basically, a compound having an asymmetric carbon bonded to a basic group capable of coordinating to the metal on the porphyrin ring of said metalloporphyrin dimer or an asymmetric carbon adjacent to the carbon atom bonded to said basic group (i.e., an asymmetric carbon bonded to the carbon atom having the basic group). In the metalloporphyrin dimer, one porphyrin ring has at least one ethyl or substituent bulkier than ethyl and the other porphyrin ring bonded thereto has a metal.

Representative examples of such basic groups are amino and hydroxyl. More specifically, the chiral compound whose absolute configuration can be determined by the method of the present invention is a compound which forms a ligand for a metalloporphyrin. Representative examples of chiral compounds are 1) primary amines, 2) secondary amines, 3) primary diamines, 4) secondary diamines, 5) monoalcohols, and 6) aminoalcohols.

For example, all the compounds listed in Table 1 from 2-buthanol to N-methyl-1-phenylethylamine correspond to chiral compounds having an asymmetric carbon bonded to a basic group capable of coordinating to the metal of the porphyrin ring. 2-methyl-1-butylamine corresponds to a chiral compound having an asymmetric carbon adjacent to the carbon atom bonded to the coordinative basic group.

With respect to compounds having 2 or more asymmetric carbons such as bornylamine and diamine shown in Table 1, the absolute configuration of the asymmetric carbon bonded to the amino group coordinated to the metal of the metalloporphyrin can be determined.

In the present invention, the chiral compound capable of forming a ligand for a metalloporphyrin is coordinated to the metalloporphyrin, preferably in a non-ligand-forming solvent, and the resulting coordination compound is analyzed by CD spectrophotometry.

That is, the new method of the present invention for determining the absolute configuration of a variety of chiral compounds capable of coordination to metalloporphyrins comprises analyzing a mixed sample of a chiral compound and a metalloporphyrin in a non-ligand solvent, by circular dichroism (CD) spectrophotometry. According to this method, the absolute configuration of chiral compounds can be directly observed without the need to derive any specifically modified compounds, and the chirality of the carbon atom directly bonded to the ligand-forming group or a carbon atom adjacent to the carbon atom can be determined.

Representative examples of non-ligand solvents include halogenated aliphatic hydrocarbons such as chloroform ($CHCl_3$), dichloride methane ($CH_2Cl_2$), dichloride ethane ($CH_2ClCH_2Cl$), tetrachloride ethane ($CHCl_2CHCl_2$), carbon tetrachloride ($CCl_4$) and the like, and aliphatic hydrocarbons such as hexane, heptane and the like.

In the method of the present invention, samples to be analyzed by CD spectrophotometry can be prepared, for example, in the following manner:

A chiral compound and a metalloporphyrin are dissolved in said solvent. The concentrations of the chiral compound and the metalloporphyrin are not critical. Generally, the concentration of the chiral compound should be $10^{-4}$ mol/l or higher, and the concentration of the metalloporphyrin $10^{-6}$ mol/l or higher. Their concentrations can suitably be selected from the above ranges in accordance with the type of solvent used, etc.

In the case of the metalloporphyrin of formula (1), the minimum concentrations of chiral compounds required for observing sufficient Cotton effects are as follows: primary acyclic monoamines preferably have a minimum concentration of about $10^{-3}$ mol/l, cyclic aromatic monoamines about $10^{-4}$ mol/l, secondary amines about $10^{-4}$ mol/l, diamines about $10^{-3}$ mol/l and aminoalcohols about $10^{-3}$ mol/l. Preferably, the minimum concentration of monoalcohols required for observing sufficient Cotton effects is about $10^{-1}$ mol/l and the temperature is $-80°$ C.

The following cases 1-5 can be mentioned as examples.

[Case 1]

The absolute chirality of primary monoamines can preferably be determined when the minimum concentration thereof in chloroform, dichloromethane, carbon tetrachloride, tetrachloroethane, hexane or heptane is adjusted to about $10^{-4}$ mol/l to $10^{-3}$ mol/l and the concentration of the metalloporphyrin of formula (I) is about $10^{-6}$ mol/l. Examples of primary monoamines include 2-butylamine, 1-phenylethylamine, 1-(1-naphtyl)ethylamine, 1-cyclohexylethylamine, 2-methyl-1-butylamine, and [endo-(1R)-1,7,7-trimethylbicyclo[2,2,1]heptan-2-amine].

[Case 2]

The absolute chirality of secondary monoamines can preferably be determined when the minimum concentration thereof in chloroform, dichloromethane, carbon tetrachloride, tetrachloroethane, hexane or heptane is adjusted to about $10^{-4}$ mol/l and the concentration of the metalloporphyrin of formula (I) is about $10^{-6}$ mol/l. Examples of secondary monoamines include N-methyl-1-phenylethylamine.

[Case 3]

The absolute chirality of diamines can preferably be determined when the minimum concentration thereof in chloroform, dichloromethane, carbon tetrachloride, tetrachloroethane, hexane or heptane is adjusted to about $10^{-3}$ mol/l and the concentration of the metalloporphyrin of formula (I) is about $10^{-6}$ mol/l. Examples of diamines include 1,2-diphenylethylenediamine and 1,2-diaminocyclohexane.

[Case 4]

The absolute chirality of aminoalcohols can preferably be determined when the minimum concentration thereof in chloroform, dichloromethane, carbon tetrachloride, tetrachloroethane, hexane or heptane is adjusted to about $10^{-3}$ mol/l and the concentration of the metalloporphyrin of formula (I) is about $10^{-6}$ mol/l. Examples of aminoalchols include 1-amino-2-propanol and 2-amino-4-methyl-1-pentanol.

[Case 5]

The absolute chirality of monoalcohols can preferably be determined when the minimum concentration thereof is adjusted to about $10^{-1}$ mol/l and the concentration of the metalloporphyrin of formula (I) is about $10^{-6}$ mol/l in dichloromethane or hexane at $-80°$ C. Examples of monoalcohols include 2-butanol and 1-phenylethanol.

The present invention enables precise and easy determination of the absolute configuration of chiral compounds having a wide variety of basic groups bonded thereto. That is, the method of the invention can precisely and easily determine the absolute configuration of the chiral compounds having an asymmetric carbon directly bonded to a coordinative basic group or an asymmetric carbon adjacent to the carbon atom bonded to the basic group. More specifically, the method of the present invention achieves the following excellent effects:

1) The absolute chirality of various optionally active compounds can be directly observed.
2) Only trace amounts of samples, i.e., metalloporphyrin (at the level of μg) and chiral compounds (amines (μg), alcohols (mg)) are needed.
3) Since no chemical change occurs, the samples can be recovered easily, if necessary.
4) Determination of absolute chirality is very fast. Preparation of the samples and measurement of the CD spectra can be done in 10 minutes.
5) The detection of Cotton effects is usually carried out in the region of 400 to 450 nm, while most chiral compounds have absorptions up to 400 nm. Therefore, a wide variety of compounds can be analyzed.
6) The chiral compounds can be used without the need to derive any specifically modified compounds.
7) The absolute chirality of non-crystalline compounds can be determined.

BEST MODE FOR CARRYING OUT THE INVENTION

The present invention will be described below in further detail with reference to an Example.

EXAMPLE 1

Figure 4:
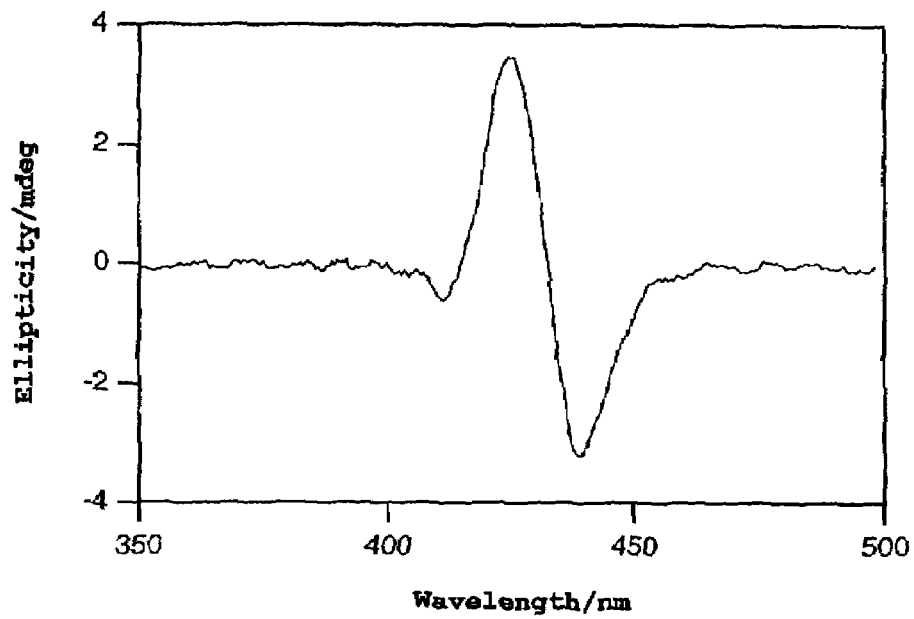
FIG. 4 shows CD spectra obtained using (R)-(−)-1-cyclohexylethylamine in the Example.

A $CH_2Cl_2$ solution containing about $10^{-6}$ mol/l of zinc porphyrin of formula (I) and about $10^{-4}$ mol/l of (R)-(−)-1-cyclohexylamine was prepared in a 3 ml cell, and the circular dichroism spectra were observed in the region of 350 nm to 500 nm at room temperature. FIG. 4 shows the results.

The absolute configuration of a chiral compound is determined from the sign of the first Cotton effect at a longer wavelength. From the negative sign of the first Cotton effect as shown in FIG. 4, the absolute configuration of (R)-(−)-1-cyclohexylethylamine was confirmed to be (R).

Figure 5:
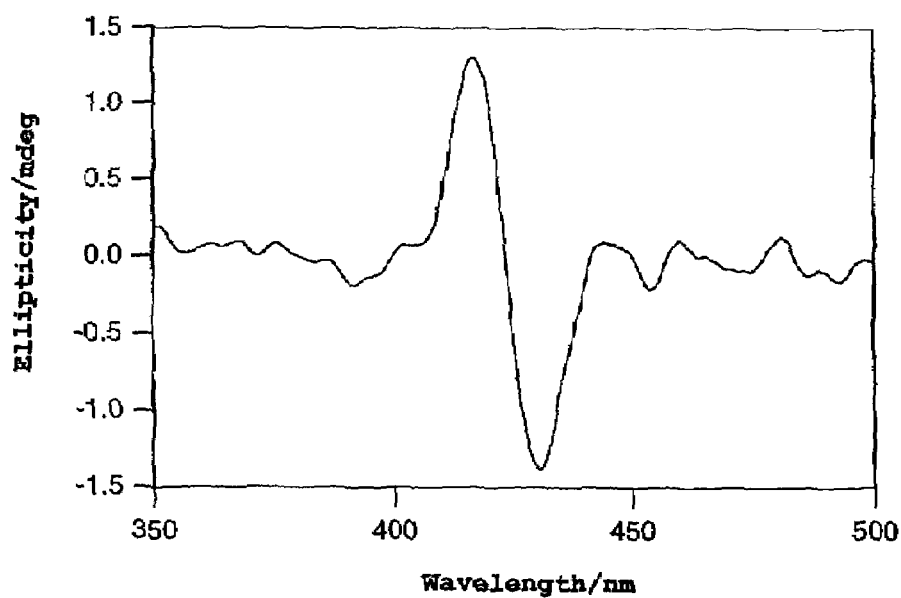
FIG. 5 shows CD spectra obtained using (R)-(−)-phenylethanol in the Example.

Similarly, a $CH_2Cl_2$ solution containing about $10^{-6}$ mol/l of the zinc porphyrin and about $10^{-1}$ mol/l of (R)-(−)-1-phenylethanol was prepared in a 3 ml cell, and the circular dichroism spectra were observed in the region of 350 nm to 500 nm at −80° C. FIG. 5 shows the results.

In this case also, the sign of the first Cotton effect was negative. Thus the absolute configuration of the chiral compound was confirmed to be (R).

The method of the present invention determines the absolute configuration of chiral compounds in the manner described above. The effectiveness of this method was also confirmed for the assignment of the absolute configuration of chiral amines and alcohols as shown in Table 1.

The invention claimed is:

1. A method for determining the absolute configuration of a chiral compound which comprises:
   coordinating the chiral compound to a metalloporphyrin represented by the following formula (I):

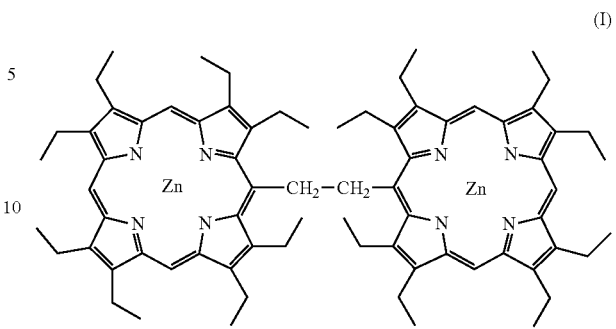

(I)

{μ{{5,5'- (ethane-1, 2-diyl) bis [2, 3, 7, 8, 12, 13, 17, 18-octaethyl-21H, 23H-porphyrinato](4-)}-κN$^{21}$, -κN$^{22}$, -κN$^{23}$, -κN$^{24}$, -κN$^{21'}$, -κN$^{22'}$, -κN$^{23'}$, -κN$^{24'}$, }}dizinc, the chiral compound having an asymmetric carbon bonded to a basic group capable of coordinating to the metal of the other porphyrin ring of the metalloporphyrin dimer or an asymmetric carbon atom adjacent to the carbon atom bonded to the basic group; and analyzing the resultant coordination compound by circular dichroism spectrophotometry to determine the absolute configuration of the asymmetric carbon of the chiral compound based on the sign of the Cotton effect, wherein when the first Cotton effect is positive, the absolute configuration of the chiral compound is (S), and when the first Cotton effect is negative, the absolute configuration of the chiral compound is (R).

2. The method according to claim 1 wherein the chiral compound is 1) a primary amine, 2) a secondary amine, 3) a primary diamine, 4) a secondary diamine, 5) a monoalcohol, or 6) an aminoalcohol.

* * * * *